United States Patent [19]

Perine et al.

[11] Patent Number: 5,120,873

[45] Date of Patent: Jun. 9, 1992

[54] PROCESS FOR PREPARING SOLID BETAINES

[75] Inventors: Jeffrey W. Perine; Joe D. Sauer; Kim R. Smith; James E. Borland, all of Baton Rouge, La.

[73] Assignee: Ethyl Corporation, Richmond, Va.

[21] Appl. No.: 723,976

[22] Filed: Jul. 1, 1991

[51] Int. Cl.$^5$ .......................................... C07C 229/00
[52] U.S. Cl. .................... 562/575; 562/443; 562/444; 562/553; 562/567
[58] Field of Search ............... 562/575, 567, 553, 443, 562/444

[56] References Cited

U.S. PATENT DOCUMENTS

| | | | |
|---|---|---|---|
| 2,082,275 | 6/1937 | Daimler | 562/575 |
| 2,129,264 | 9/1938 | Downing | 562/575 |
| 2,564,507 | 8/1951 | Schaeffer | 562/575 |
| 2,800,502 | 7/1957 | Uassel | 562/575 |
| 3,480,665 | 11/1969 | Nagy | 562/575 |
| 3,555,079 | 1/1971 | Murumo | 260/501.13 |
| 3,649,677 | 3/1972 | Morris | 562/575 |
| 3,954,845 | 5/1976 | Martinsson | 562/575 |
| 4,832,871 | 5/1989 | Bade | 252/546 |

FOREIGN PATENT DOCUMENTS 1185111 3/1970 United Kingdom .

OTHER PUBLICATIONS

Nandakumar, "Journal of the Oil Technologists' Association of India", vol. 11(2), pp. 31–34 (1979).

Primary Examiner—Michael L. Shippen
Attorney, Agent, or Firm—Patricia J. Hogan

[57] ABSTRACT

Betaines are produced in solid form by reacting a tert-amine with a haloalkanoate salt when the reaction is conducted in a liquefied gas as the solvent. In a preferred embodiment, the tert-amine is an N-alkyldimethylamine, the haloalkanoate is sodium chloroacetate, and the liquefied gas is carbon dioxide.

11 Claims, No Drawings

PROCESS FOR PREPARING SOLID BETAINES

FIELD OF INVENTION

This invention relates to a process for preparing solid betaines by reacting a tert-amine with a haloalkanoate salt.

BACKGROUND

As disclosed in British Patent 1,185,111 (Morris) and U.S. Pat. Nos. 2,082,275 (Daimler et al.), 3,555,079 (Marumo et al.), and 4,832,871 (Bade), it is known that tert-amines can be quaternized with haloalkanoate salts in water or a polar aprotic solvent to prepare betaines in solution form, most commonly as 30–35% active aqueous solutions.

Solid betaines have the advantages over betaine solutions that they can be transported at lower costs and offer more flexibility in the formulation of products from betaines. It is possible to recover solid betaines from the solutions, but it would be preferable to be able to prepare the betaines directly in solid form.

Copending application Ser. No. 07/652,617 (Perine et al.), now U.S. Pat. No. 5,075,498, discloses a process whereby betaines are prepared in solid form by reacting tert-amines with haloalkanoate salts in polar aprotic solvents in which the betaines are substantially insoluble. This process is a commercially-attractive method of producing betaines. However, when it is used to prepare a substantially pure betaine, it requires the use of centrifugation, crystallization, and drying steps which add to its cost.

SUMMARY OF INVENTION

It has now been found that betaines can be more economically produced in solid form by the reaction of a tert-amine with a haloalkanoate salt when the reaction is conducted in a liquefied gas as the solvent.

DETAILED DESCRIPTION

As evidenced by the variety of types of tert-amines which have been quaternized with haloalkanoates in the past, the particular tert-amine used in the process is not critical. It may be, e.g., any of the tert-amines of Morris, Daimler et al., Marumo et al., and Bade.

The tert-amines which are generally most valuable to employ in the reaction are those in which at least one of the N-substituents is an alkyl or hydroxyalkyl group and the remaining N-substituents are aliphatic or cyclic organic groups which may be hydrocarbyl or non-hydrocarbyl in nature, e.g., alkyl, hydroxyalkyl, polyoxyethylene, alkylamidoalkyl, phenyl, or benzyl, including those in which an alkyl or hydroxyalkyl group is attached to a nitrogen which is a member of a heterocyclic ring, such as a morpholine ring.

Among the preferred tert-amines are the compounds corresponding to the formula $RR'R''N$ in which R is a linear or branched-chain alkyl group containing 6–22 carbons, more preferably a primary alkyl group containing 8–18 carbons; R' is methyl, ethyl, or 2-hydroxyethyl; and R'' is independently selected from methyl, ethyl, 2-hydroxyethyl, and linear and branched-chain alkyl groups containing 6–22 carbons. These tert-amines may be used alone or in combination to provide, e.g.:

(1) a single $RR'R''N$ amine in which R is either a linear or a branched-chain alkyl group containing a given number of carbons, (2) a mixture of $RR'R''N$ amines in which the R of one component of the mixture is a linear alkyl group containing a given number of carbons and the R of another component of the mixture is a branched-chain alkyl group containing the same number of carbons, (3) a mixture of $RR'R''N$ amines in which the R of one component of the mixture is a linear alkyl group containing a given number of carbons and the R of another component of the mixture is a linear alkyl group containing a different number of carbons, or (4) a mixture of $RR'R''N$ amines in which the R of one component of the mixture is a linear alkyl group containing a given number of carbons, the R of another component is a branched-chain alkyl group containing the same number of carbons, and the R of another component of the mixture is a linear or branched-chain alkyl group containing a different number of carbons.

The most preferred of these tert-amines are those in which at least a majority of alkyl groups in the tert-amine or tert-amine mixture are linear and R' and R'' are independently selected from methyl, ethyl, and 2-hydroxyethyl, especially those in which both R' and R'' are methyl.

The haloalkanoate which is reacted with the tert-amine to form the betaine is generally an ammonium or Group IA or IIA metal salt of an $\omega$-haloalkanoic acid in which the halo substituent is chloro, bromo, or iodo. Neither the size nor the degree of linearity of the alkanoic moiety is critical, but it is most commonly a moiety containing up to about 30 carbons and in which any branching is confined to carbons other than the carbon to which the halo substituent is attached, since any branching on that carbon could be expected to slow the reaction significantly.

Exemplary of the haloalkanoates that can be used are the sodium, potassium, lithium, rubidium, cesium, beryllium, magnesium, calcium, strontium, barium, and ammonium salts of chloroacetic, chloropropionic, chlorobutyric, chloropentanoic, chlorohexanoic, chloroheptanoic, chloro-$\beta$-ethylhexanoic, and corresponding bromo- and iodoalkanoic acids. The preferred haloalkanoates are compounds corresponding to the formula $X(CH_2)_nCOOM$ in which X is chloro, bromo, or iodo; M is alkali metal or ammonium; and n is an integer of 1–6. As in conventional processes, the most preferred haloalkanoate is sodium chloroacetate.

The amount of haloalkanoate employed to quaternize the tert-amine is usually at least the stoichiometric amount. However, to reduce contamination of the product with excess haloalkanoate which might have to be removed by solvent extraction at the end of the reaction, it is preferred not to use too much of the haloalkanoate reactant. Thus, it is generally preferable to utilize the reactants in substantially stoichiometric amounts.

The liquefied gas used as the reaction medium in the process may be the liquefied form of any normally gaseous material which is inert in the sense that it will neither prevent the reaction from occurring nor react with the product. Such normally gaseous materials include, e.g., air, oxygen, carbon dioxide, nitrogen, argon, ethylene, methane, ethane, propane, butane, isobutane, trifluoromethane, tetrafluoromethane, chlorotrifluoromethane, and mixtures thereof. Carbon dioxide is sometimes preferred.

Most commonly, the liquefied gas which is employed is one that is commercially available and can simply be introduced into the reaction vessel in liquid form and maintained in liquid form by the use of pressure. However, if desired, it may be acquired in the gaseous state and introduced into the reaction vessel via a compressor to liquefy it.

Because of the greater expense involved in liquefying a gas which has a very low critical temperature, it is frequently preferred to employ as the liquefied gas a normally gaseous material which has a critical temperature that is above or not much below room temperature, generally a critical temperature of at least 0° C., preferably at least 20° C., e.g., materials such as ethylene, carbon dioxide, chlorotrifluoromethane, ethane, propane, butane, and isobutane.

The process of the invention is conducted by combining the tert-amine with at least a portion of the haloalkanoate salt in the liquefied gas solvent and allowing the quaternization reaction to occur. It is generally preferred to include all of the haloalkanoate and all of the solvent in the initial reaction mixture, but satisfactory results can also be obtained when the salt is gradually added in increments and/or a portion of the solvent is fed into the reactor after the reaction has commenced. If desired, some preformed betaine product may also be included in the initial reaction mixture to shorten the time before which any noticeable quaternization occurs.

Although the reaction can be effected at room temperature, it is ordinarily preferred to use an elevated temperature, preferably a temperature in the range of about 50°-150° C., to speed the reaction. The process is conducted under a pressure sufficient to maintain the liquefied gas in the liquid state, and pressures in excess of the minimum requirements can be used if desired. Most commonly, the amount of pressure used is chosen to be consistent with conducting an economical process, usually a pressure in the range of about 4.9-8.5 MPa.

In general, the reaction may be conducted so as to have supercritical or subcritical conditions.

The quaternization may be accomplished by a batch, semibatch, or continuous process in the presence of the liquefied gas, which is vented from the reaction vessel after completion of the reaction. Because of the use of the liquefied gas as the sole solvent, the solid betaine product remaining after the venting of the system can be recovered without the need for the crystallization, centrifugation, and drying steps required in earlier betaine syntheses unless it is desired to remove the salts that remain with the product. Thus, the process of the invention is an economically-advantageous method of preparing solid betaines.

What is claimed is:

1. In a process for preparing a betaine by reacting a tert-amine with a haloalkanoate salt, the improvement which comprises conducting the reaction in a liquefied gas as the solvent.

2. The process of claim 1 wherein the tert-amine is a compound corresponding to the formula RR'R"N in which R is an alkyl group containing 6-22 carbons; R' is methyl, ethyl, or 2-hydroxyethyl; and R" is independently selected from methyl, ethyl, 2-hydroxyethyl, and alkyl groups containing 6-22 carbons.

3. The process of claim 2 wherein R is a primary alkyl group containing 8-18 carbons and R' and R" are independently selected from methyl, ethyl, and 2-hydroxyethyl.

4. The process of claim 3 wherein R' and R" are methyl.

5. The process of claim 2 wherein R and R" are independently selected from primary alkyl groups containing 8-18 carbons.

6. The process of claim 5 wherein R' is methyl.

7. The process of claim 1 wherein the haloalkanoate is a compound corresponding to the formula $X(CH_2)_nCOOM$ in which X is chloro, bromo, or iodo; M is alkali metal or ammonium; and n is an integer of 1-6.

8. The process of claim 7 wherein the haloalkanoate is sodium chloroacetate.

9. The process of claim 1 wherein the liquefied gas is a gas which has a critical temperature of at least 0° C.

10. The process of claim 9 wherein the liquefied gas has a critical temperature of at least 20° C.

11. The process of claim 10 wherein the liquefied gas is carbon dioxide.

* * * * *